(12) United States Patent
Fletcher

(10) Patent No.: US 6,971,993 B2
(45) Date of Patent: Dec. 6, 2005

(54) METHOD FOR UTILIZING ORAL MOVEMENT AND RELATED EVENTS

(75) Inventor: Samuel G. Fletcher, Springville, UT (US)

(73) Assignee: Logometrix Corporation, Glendale, AZ (US)

( * ) Notice: Subject to any disclaimer, the term of this patent is extended or adjusted under 35 U.S.C. 154(b) by 399 days.

(21) Appl. No.: 09/991,329

(22) Filed: Nov. 14, 2001

(65) Prior Publication Data

US 2002/0087322 A1 Jul. 4, 2002

Related U.S. Application Data

(60) Provisional application No. 60/249,148, filed on Nov. 15, 2000.

(51) Int. Cl.[7] ............ A61B 5/103; A61F 5/58; G09B 19/04
(52) U.S. Cl. .......... 600/587; 600/590; 600/23; 434/185
(58) Field of Search ............ 600/23, 24, 587, 600/590, 595; 434/185; 704/200, 276

(56) References Cited

U.S. PATENT DOCUMENTS

| | | |
|---|---|---|
| 3,349,489 A | 10/1967 | Shackelford |
| 3,524,932 A | 8/1970 | Stucki |
| 3,752,929 A | 8/1973 | Fletcher |
| 3,983,865 A | 10/1976 | Shepard |
| 4,052,799 A | 10/1977 | Journot |
| 4,112,596 A | 9/1978 | Fletcher et al. |
| 4,175,338 A | 11/1979 | Takinishi et al. |
| 4,287,895 A | 9/1981 | Hori |
| 4,310,002 A | 1/1982 | Takinishi et al. |
| 4,334,542 A | 6/1982 | Takinishi et al. |
| 4,460,342 A | 7/1984 | Mills |
| 4,520,501 A | 5/1985 | DuBrucq |
| 4,672,673 A | 6/1987 | Katz et al. |
| 4,697,601 A | 10/1987 | Durkee et al. |
| 4,784,115 A | 11/1988 | Webster |
| 4,907,602 A | 3/1990 | Sanders |
| 4,980,917 A * | 12/1990 | Hutchins ............... 704/254 |
| 5,016,647 A | 5/1991 | Sanders |
| 5,169,316 A | 12/1992 | Lorman et al. |
| 5,212,476 A | 5/1993 | Maloney |
| 5,213,553 A | 5/1993 | Light |
| 5,257,930 A | 11/1993 | Blakeley |

(Continued)

FOREIGN PATENT DOCUMENTS

JP 50-001846 1/1975

(Continued)

OTHER PUBLICATIONS

Fletcher, Samuel G., Articulation a Physiological Approach, Singular Publishing Group, Inc., 1992.*

(Continued)

*Primary Examiner*—Charles Marmor
(74) *Attorney, Agent, or Firm*—Clayton, Howarth & Cannon, P.C.

(57) ABSTRACT

A method for utilizing oral movements is used in speech assessment, speech therapy, language development, and controlling external devices. A device is used which includes a sensor plate having sensors to detect contact of the tongue with the sensor plate. One aspect of the invention allows viewing representations of contact of the tongue and palate during speech and comparing the representations with model representations displayed in a split screen fashion. The model representations may be generated by another speaker utilizing a sensor plate or by computer generated representations which have been electronically stored. The representations may be analyzed to assess speech proficiency and the model may be mimicked for speech enhancement.

37 Claims, 3 Drawing Sheets

U.S. PATENT DOCUMENTS

| | | | |
|---|---|---|---|
| 5,326,349 A | 7/1994 | Baraff | |
| 5,340,316 A | 8/1994 | Javkin et al. | |
| 5,393,236 A | 2/1995 | Blackmer et al. | |
| 5,452,727 A | 9/1995 | Tura et al. | |
| 5,487,671 A | 1/1996 | Shpiro et al. | |
| 5,536,171 A * | 7/1996 | Javkin et al. | 434/185 |
| 5,609,161 A | 3/1997 | Tura et al. | |
| 5,689,246 A | 11/1997 | Dordick et al. | |
| 5,794,203 A | 8/1998 | Kehoe | |
| 5,813,862 A | 9/1998 | Merzenich et al. | |
| 5,913,188 A | 6/1999 | Tzirkel-Hancock | |
| 5,954,673 A | 9/1999 | Staehlin et al. | |
| 6,343,269 B1 | 1/2002 | Harada et al. | |
| 6,430,450 B1 | 8/2002 | Bach-y-Rita et al. | |
| 6,447,299 B1 * | 9/2002 | Boon | 434/156 |

FOREIGN PATENT DOCUMENTS

| | | |
|---|---|---|
| JP | 50-11505 | 2/1975 |
| JP | 53-42490 | 4/1978 |
| JP | 53-47193 | 4/1978 |
| JP | 55-131207 | 9/1980 |
| JP | 55-143146 | 11/1980 |
| JP | 55-148554 | 11/1980 |
| JP | 58-150995 | 9/1983 |
| JP | 58-150997 | 9/1983 |
| JP | 01260481 A | 10/1989 |

OTHER PUBLICATIONS

S. Awad. The Application of Digital Speech Processing to Stuttering Therapy. IEEE Instrumentation and Measurement, 1997, pp. 1361-1367.

S. Awad. Computer Assisted Treated for Motor Speech Disorders. IEEE, 1999, pp. 595-600.

V. Georgopoulos. An Investigation of Audio-Visual Speech Recognition as Applied to Multimedia Speech Therapy Applications. IEEE, 1999, pp. 481-486.

J. G. Hochberg et al. An Animated Display of Tongue, Lip and Jaw Movements During Speech: A Proper Basis for Speech Aids to the Handicapped and Other Speech Technologies. IEEE, 1992, pp. 57-59.

S. Hutchins. Say & See: Articulation Therapy Software. IEEE, 1992, pp. 37-40.

A. McMahon. The Clinical Use of Nasometry (Kay Elemetrics Nasometer-Model 6200-3), pp. 1-3.

Nasometer II, Model 6400, The Most Widely Used Clinical Tool for Assessment and Treatment of Nasality Problems, pp. 1-2.

UCLA Phonetics Lab, Electropalatography (EPG), pp. 1-14.

S. Yamaguchi et al. A Basic Study on Talking Aid and Voice Clarification for the Hearing Disorder Persons, IEEE, 1999, pp. 358-363.

* cited by examiner

METHOD FOR UTILIZING ORAL MOVEMENT AND RELATED EVENTS

CROSS-REFERENCE TO RELATED APPLICATIONS

This application claims the benefit of U.S. Provisional Application No. 60/249,148, filed Nov. 15, 2000.

STATEMENT REGARDING FEDERALLY SPONSORED RESEARCH OR DEVELOPMENT

Not Applicable.

BACKGROUND OF THE INVENTION

1. The Field of the Invention

The present invention relates generally to methods of using oral movements, and more particularly, but not necessarily entirely, to methods of using movement of the tongue for providing speech therapy and speech assessment.

2. Description of Related Art

Speech is defined herein as the outcome of a biologically based propensity to imitate vocal gestures and sound patterns in communication development. The notion that humans use an inborn scheme, process, or representation to assimilate and organize phonological functions and to guide sound perception and production underpins the disclosure herein. This conceptualization, identified as the endogenous image mimicry (EIM) hypothesis, is supported by prior findings from infant facial and vocal imitation, phonetic categorical perception, oral structure and function maturation, and optimum sound production observations.

Studies of infant neonates have shown that babies imitate gestures such as mouth opening, tongue protrusion, and vowel-like utterances from early infancy without practice or trial and error.

Speech developmental accounts seem to assume that hearing plays a virtually exclusive role in sound mimicry and speech learning. This viewpoint is supported by the observation that children with severe to profound hearing losses show major speech deficits from early infancy. The potential utility of vision in phonetic mimicry and sound learning has been clouded, however, by the inaccessibility of viewing most speech actions. Speech relevant acts such as early facial gesture and labial sound mimicry are in fact present in the responses of children with even profound hearing losses. Such findings suggest that vision could play an important role in later speech mimicry and articulatory learning if the learner could be given access to the normally hidden articulation gestures and actions.

In the late 1800s phoneticians discovered that they could visualize sound production patterns by coating the palate with powder, having the person speak, then sketching or photographing where the tongue made contact and removed the powder. The tongue-palate contact patterns were claimed to be distinctive regardless of individual subject differences. Saying a second sound, however, was noted to destroy the linguapalatal wipe pattern. This effect became quickly problematic when attempts were made to use this palatographic procedure in speech sound modification. For example, Barker (Journal of Speech Disorders, 2, p 165) reported that the Abbe Rousselot made "extensive use" of palatography to determine and correct articulator position. He was not successful, however, in his efforts to eliminate the English accent in French spoken by a single person during his five-year period of trials. Dynamic speech production thus remained physically inscrutable and the use of palatographic technology for speech training faded away.

The 1950s and 60s brought a serious search for new ways to expose the dynamic nature of speech. Cineradiology provided a possible doorway but difficulties incident to the dangerous radiation inherent in x-ray exposure as well as problems with key frame selection, slow and arduous hand tracing, noise that obscured acoustic details and soft tissue concealment behind bony structures severely restricted its speech remedial use. Computerized x-ray microbeam systems reduced the radiation, but this complex and expensive technology limited the diagnostic observations to a few points that could be tracked simultaneously. And radiation, though reduced, still blocked its use in speech remediation. In the 1980s magnetic resonance imaging brought body-sectioning principles to speech studies but its cost and technical difficulties such as the need for the subjects to be in a supine position limited its remedial speech use. The limitation of the information to a few samples per second also discouraged its use in speech.

Palatographic observations were reintroduced in the 1960s using electronic technology to overcome the single-sound observation limitations. Kusmin (Forth International Congress on Acoustics, Copenhagen, Report G35) in Russia used paired electrodes to detect linguapalatal contact. Although both of the electrodes needed to be contacted simultaneously to complete the circuit, several other investigators adopted this approach. Kydd and Belt (Journal of Speech and Hearing Disorders, 29:489–492) introduced a different palatographic approach. They used the tongue as the positive pole in a battery analog with twelve electrodes serving to detect linguapalatal contact. Both the Kusmin and Kydd-Belt systems were fraught with signal detection and sensor-to-sensor saliva bridging problems.

In 1969 Fletcher, Berry, and Greer (see U.S. Pat. No. 4,112,596, granted Sep. 12, 1978 to Fletcher et al.) introduced the use of an AC signal to inject an imperceptible current into the body. The current flowed from its source to and through the tongue to sensors on a 48-electrode "pseudopalate." Their technology succeeded in virtually eliminating saliva bridging difficulties and enabled Fletcher and other associates to increase the number of pseudopalate sensors to 96.

Since speech represents the output from a complex biological and phonological system, multiple sources of articulatory deviation may be expected. A long accepted general hypothesis among speech pathologists is that articulatory disorders are products of experiential and physical conditions that block a learner from achieving normal sound production proficiency. Several tests and measures, as described below, have been developed to help pinpoint possible sources of such deviations.

a) Target to Target Tongue Placement and Motor Control.

Observations since the early 1980's suggest that speakers plan and control motor movements to phonetically dictated target positions by using an internal spatial representation or cognitive topological map. To what degree a person is capable of discovering specific strategies during speech development that help them bypass or overcome structural and/or functional irregularities is still speculative. For example, certain deviations may block full use of a speaker's cognitive map. A more rapid speaking rate and reduced variability across age evidences increased motor skills with maturation. Such increased motor skill would also be expected to help a speaker overcome physical deficits. On the other hand, Smith and Goffman (Journal of Speech, Language, and Hearing Research, 41:18–30) suggest that higher variability at younger ages may be beneficial. It could be a sign of greater neural network plasticity that would help children adapt to their rapidly changing oral structures during the developmental years.

Disturbances at different locations within the motor control system may be hypothesized to signal unique disruptions in the movement actions and in the precision of goal posture achievement within the oral cavity. Due in part to past limitations in technology available to assess, differentiate, and classify oral motor disturbances, the validity of this hypothesis is conjectural at best.

b) Maximum Syllable Repetition Rate.

Maximum syllable repetition rate measures are commonly used by speech pathologists in oral/peripheral examinations to assess oral motor skill in a speech-like activity. They may also be used to help predict reduced articulation improvement as a function of subnormal oral motor skills. The rationale behind these measures is that rapid speaking and oral reading are usually carried out near a speaker's maximum sequencing rate. Errors occur increasingly as the speaker is pressed to "speed up." This articulation fragility may be used to help expose oral motor skill deficits. Such subnormal oral motor coordination would then be expected to influence speech mimicry skill.

The traditional procedure for assessing maximum syllable repetition rate (MSRR) has been to count how many consonant-vowel syllable sets, such as "pataka," a speaker can repeat in five seconds. This procedure required the examiner to count the sounds and time lapse simultaneously. Fletcher (Journal of Speech and Hearing Research, 15, 763–770) improved this procedure by introducing the "time-by-count" method. In this method the examiner starts a stopwatch, counts the set of syllables to a predetermined number, stops the watch, then reads and records the time lapse. Erroneous measures were reduced when this procedure was followed, but errors still remained a problem, particularly among novice examiners.

c) Voice Onset Time.

Interarticulator motor coordination is another important articulatory skill factor. Voice onset time (VOT), defined as the time lapse between a stop consonant articulatory release moment and the voicing onset of the following vowel, has been recognized as a sensitive index of interarticulator movement maturity. In adult spoken English, the laryngeal voicing action in voiced stop consonant production (e.g. /d/ in "do") begins at virtually the same moment as the consonant release (±20 ms). In voiceless stop consonants (e.g. /t/ in "to") the VOT is about 40 ms after the consonant release. These values vary from one language to another, but their temporal relationships are rather constant.

In view of the interstructural coordination complexity and the hidden nature of the actions involved, it is not surprising that VOT time relationships are difficult to mimic. This is indicated by their slowness to reach mature values. During early speech development virtually all stop consonants are voiced. That is, they have zero or short lag VOTs. Long lag VOT values that denote voiceless consonants emerge later, in the 2-to-6 year old age span. Neurological damage slows this developmental process. Thus, in the speech of those with cerebral palsy and dysarthria, VOT values continue to show almost exclusive use of short lag voiced stop consonants. The VOT scores of those with speech apraxia demonstrate yet a third pattern. In this condition the voiced versus voiceless consonant VOT scores overlap, reflecting oral and laryngeal motor discoordination.

Traditionally, the VOT has been measured acoustically. Attempts to derive these measures from an acoustic signal automatically have often been defeated, however, by the fact that the consonant release may produce only a brief, difficult to detect, low intensity noise. This difficulty is compounded by other noises present during the stop closure period.

d) Nonsense Word Repetition.

Nonword repetition tests have been used with increasing frequency to measure phonological memory and vocabulary knowledge. Gathercole and associates (Applied Cognitive Psychology, 13:65–67) found a strong association between phonological working memory and vocabulary in adolescents. From this observation, they suggested that phonological constraints continue to influence word learning beyond the childhood years. Linkage was also found between articulation deficits and nonsense word repetition errors.

About half of the children with impaired speech articulation have associated language impairments. This proportion rises as the children pass beyond about six years in age and many of the childhood speech disturbances become normalized. Some have speculated that the linkage between speech/language impairment and malperformance on nonword repetition tasks might reflect general processing capacity limitations in tasks that tap verbal working memory. In fact, the association between language deficits and subnormal nonsense word repetition performance appears to be so strong that subperformance on the nonsense word tests has been suggested to be a phenotype marker of inherited language impairment.

e) Phonetic Mimicry in the Older Child.

Evidence that mimicry continues to play an important role in speech refinement has been shown in auditory stimulability studies. Stimulability, defined as a person's ability to imitate a sound not present in his/her phonetic inventory, has long been used as a sound learning readiness indicator. It has been noted that early investigators used stimulability as a general predictor of the ability to correct articulation errors. More recently, investigators have tended to define it as a phoneme-specific predictor, based on the ability to imitate a sound that is absent from a child's phonetic inventory.

Pre-treatment auditory stimulability has also been used to explain post-treatment articulation generalization. For example Powel et al (Journal of Speech and Hearing Research, 34, 1318–1328) found that preschool children who misarticulate key sounds improved in production of those sounds during speech therapy regardless of the treatment targets. On the other hand, nonstimulable sounds were likely to require direct treatment. Accurate mimicry of a stimulus pattern may thus serve as an important self-correction predictor as well as a predictor of phonetic generalization and treatment responsiveness.

f) Persistent Misarticulation Modification.

Many children with childhood articulation impairments continue to experience speech difficulties into adolescence. Estimates from surveys conducted by public school speech pathologists indicate that possibly as many as 20% of the children with identified functional articulation disorders may experience persistent inability to overcome their disorders through traditional, auditory-based speech remedial procedures. That is, they fail to overcome articulation disorders despite prolonged traditional speech remedial assistance. Such persistent deficits are particularly problematic to children after they enter the teenage years. Many studies have shown that speech performance can be enhanced even among children with profound hearing loss when the traditional auditory based remedial procedures are supplemented by articulatory or sound spectrographic acoustic feedback. This suggests that children with persistent functional misarticulation could break through their articulatory learning barrier if appropriate visual articulatory or acoustic modeling and shaping routines were available to fully arouse their ability to mimic modeled articulation patterns.

The relative benefits that might be obtained from linguapalatal contact versus, or combined with, acoustic formant based visual articulatory modeling and shaping routines in remedial articulation treatment have not been previously explored. This is true notwithstanding their interdependence. Their potentially beneficial cross feedback would seems to be particularly relevant to fully identifying articulation errors, improving articulation skill generalization, and broadly helping to normalize speech skills.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY AND OBJECTS OF THE INVENTION

It is therefore an object of the present invention to provide method for utilizing lingual movements which allows speech therapy through visual modeling and mimicry.

It is another object of the invention, in accordance with one aspect thereof, to provide a method for utilizing lingual movements for speech assessment.

It is an additional object of the present invention, to provide a method for utilizing lingual movements to enhance lingual mobility.

It is a further object of the present invention, in accordance with one aspect thereof, to provide a method for utilizing lingual movements to provide speech therapy for the hearing impaired.

It is another object of the present invention to provide a method for utilizing lingual movements to develop foreign language abilities.

It is a further object of the present invention to provide a method for utilizing lingual movements to control external devices.

The above objects and others not specifically recited are realized in a specific illustrative embodiment of a method for utilizing lingual movements for providing speech therapy by displaying model representations of a position of contact between a model tongue and mouth during speech; displaying a representation of a position of contact between a learner's tongue and mouth during speech; and instructing the learner to mimic the model representations of points of contact between the model tongue and mouth during speech.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE PREFERRED EMBODIMENTS

Figure 1:
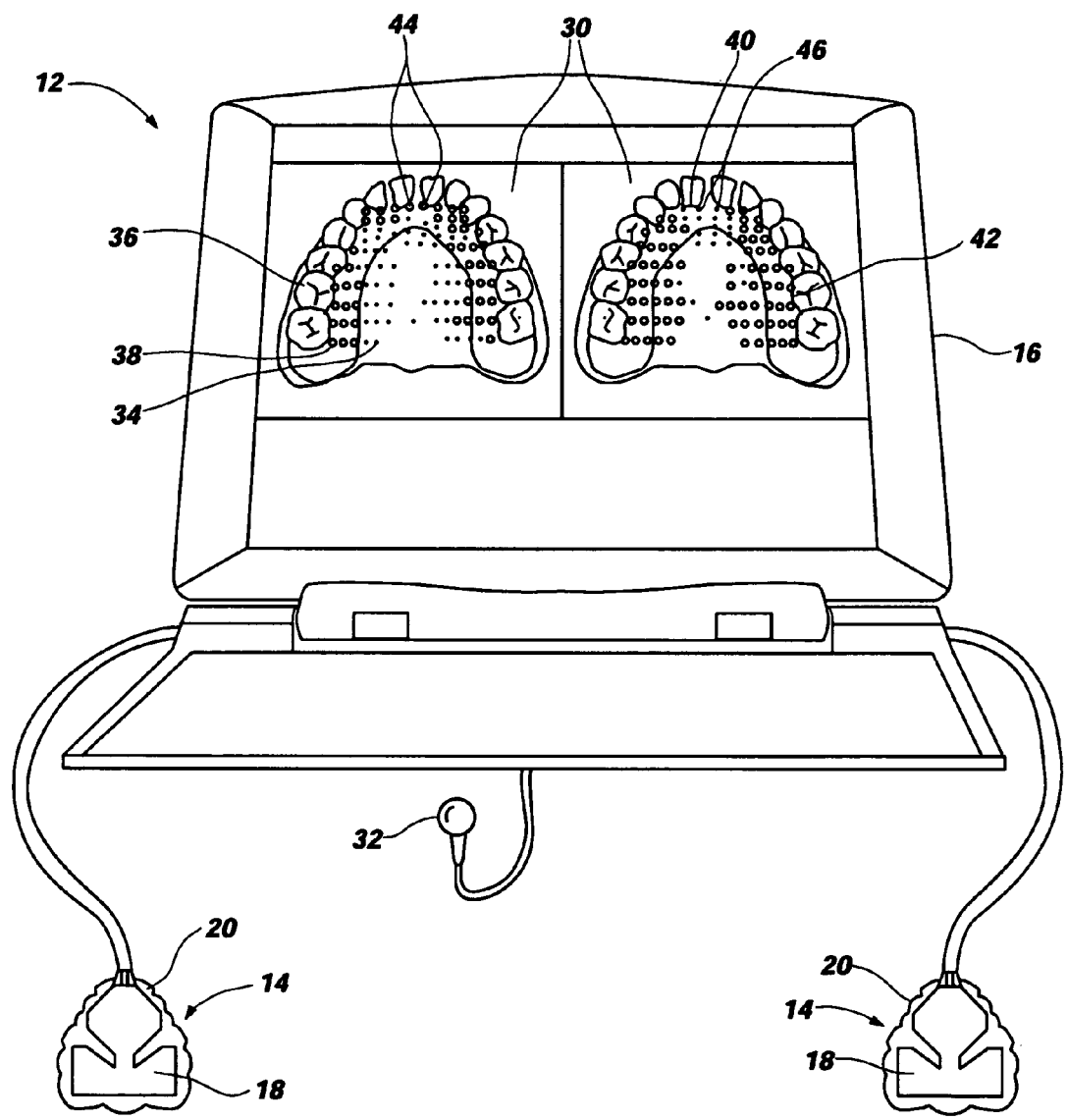
FIG. 1 is a perspective view of instrumentation used in the method in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Figure 2:
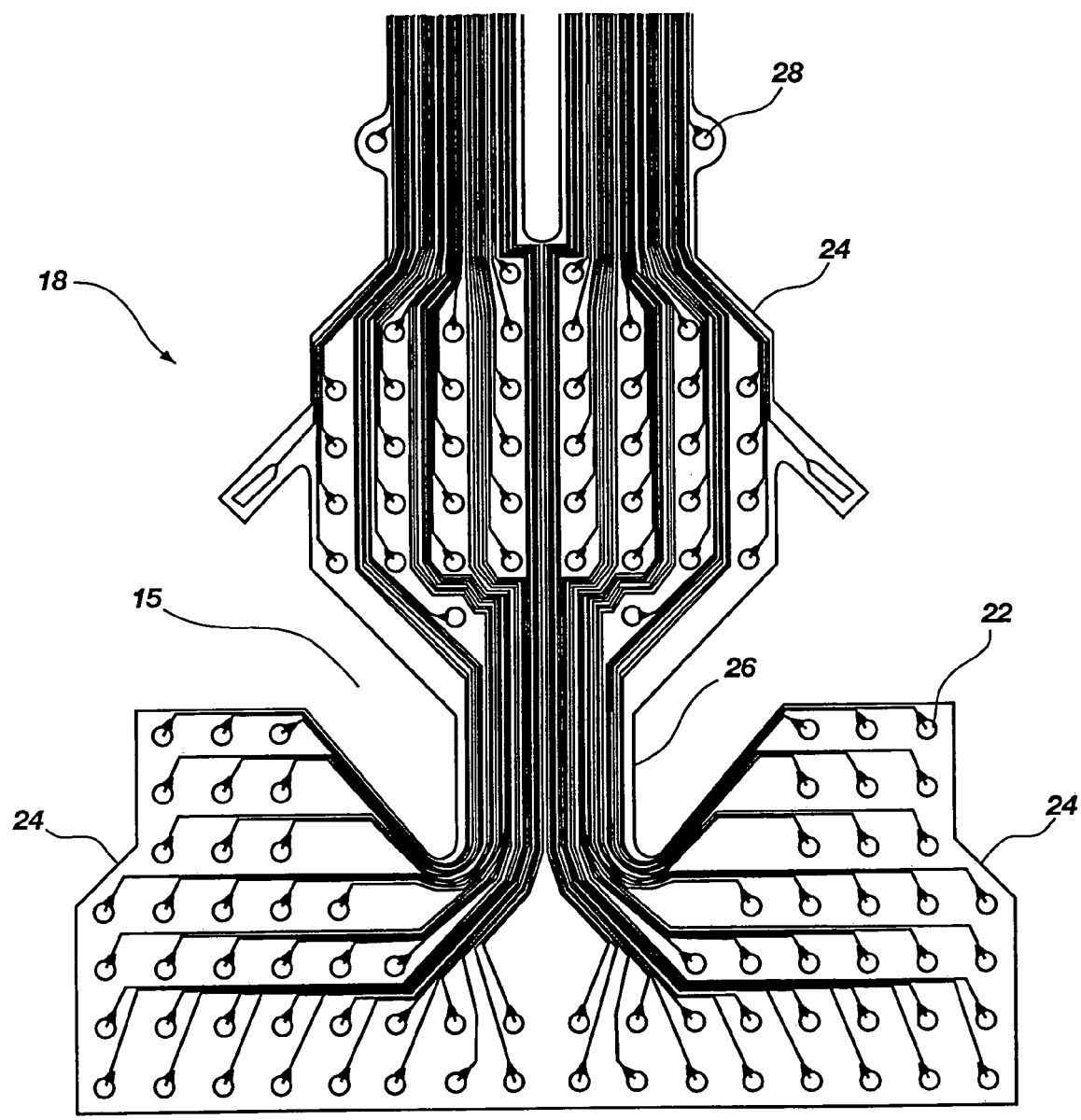
FIG. 2 is a plan view of a flexible printed circuit used in the instrumentation of FIG. 1.
Figure 3:
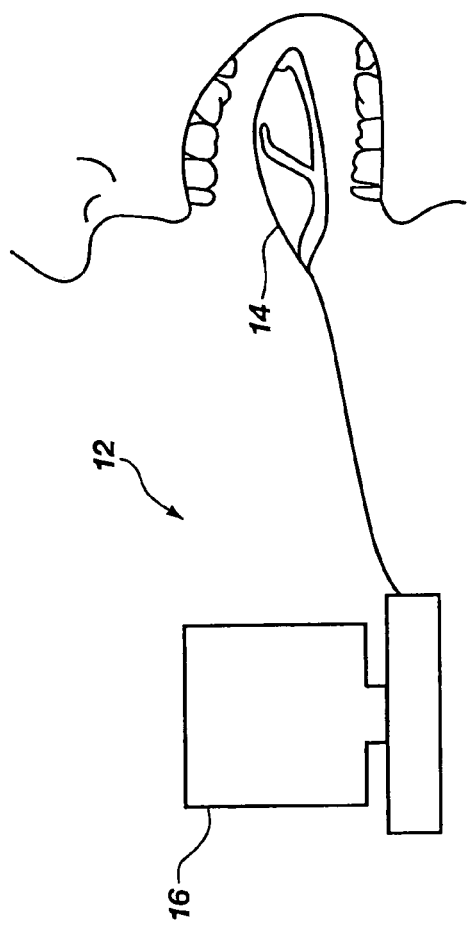
FIG. 3 is a schematic view of the instrumentation of FIG. 1, showing the sensor plate being installed in the mouth of a user.
Figure 4:
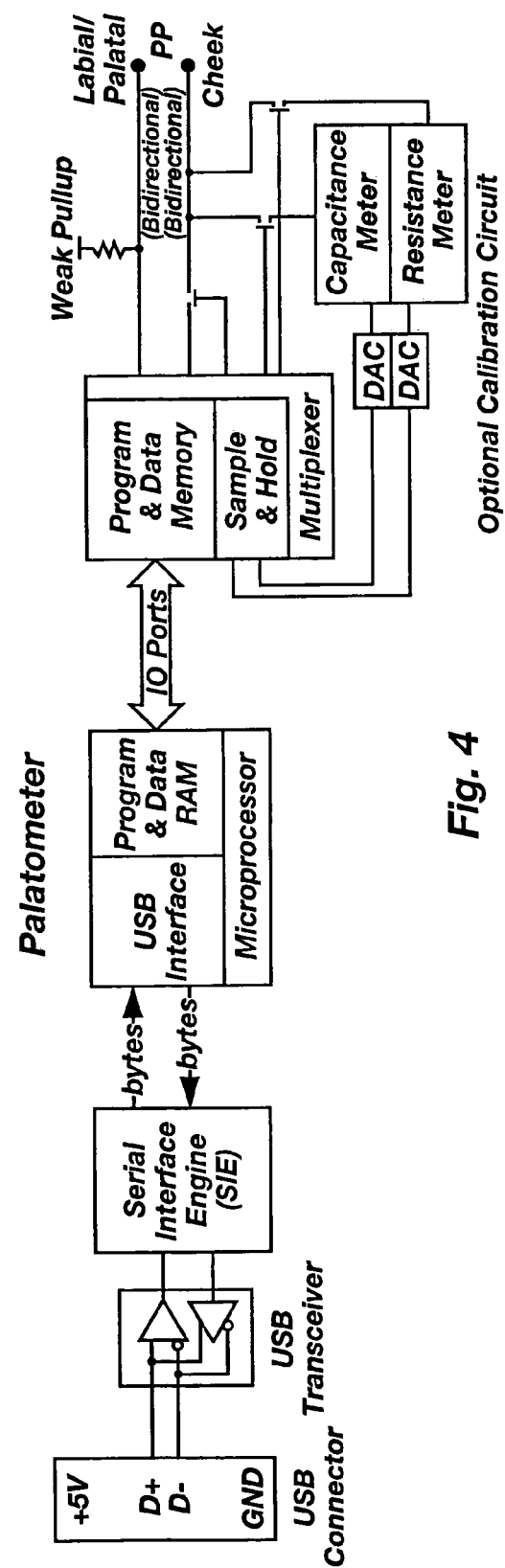
FIG. 4 is a schematic view of one of several possible embodiments of a circuit arrangement used to enable the palatometer of the present invention.

Referring now to FIG. 1, an exemplary embodiment of the instrumentation used in the methods described herein is shown. The instrumentation is more fully described in U.S. Provisional Patent Application 60/233,770 incorporated herein by reference. A palatometer 12 includes a sensor plate 14, sometimes referred to as a pseudo palate, connected to signal processing and display equipment 16. The sensor plate 14 preferably includes a flexible printed circuit 18, as best shown in FIG. 2, mounted on a baseplate 20. The flexible printed circuit 18 has contact sensing electrodes 22 distributed across its surface in a grid array. Preferably, the flexible printed circuit 18 is manufactured initially as a thin, flat plate with multiple lobes 24 intercoupled by a thin isthmus 26. This configuration allows the flexible printed circuit 18 to be adhered to a baseplate 20 which has been formed of soft plastic material to fit a user's palate and teeth configuration as shown in FIG. 3. Spaces 15 between the lobes 24 can be varied to allow the flexible printed circuit 18 to fit the curvature of the base plate 20 and at the same time retain the desired distances between sensors 22. The shape and flexibility of the flexible printed circuit 18 allows the sensor plate 14 to fit the palates of users of different sizes. The sensor plate 14 is constructed to be thin, approximately 0.5 mm, to allow a user to comfortably speak when the sensor plate 14 is installed in the user's palate. The flexible printed circuit 18 also preferably has labial sensors 28 located on the sensor plate 14 so as to reside between the incisor teeth and lips of the user when installed. Several possible embodiments of a circuit arrangement may be used to enable the palatometer of the present invention, one of which is shown in FIG. 4.

This preferred instrumentation, including palatometer 12 having the electrode sensors 22 in a standard grid pattern, enables detection, measurement, timing, and comparing of labial, linguadental, and linguapalatal contact. Contact with the electrode sensors 22 can preferably be displayed in a split screen 30 fashion. The display on one side of the screen represents contact with the electrode sensors 22 by the user.

The other side can have representations generated by computer software or another user through another sensor plate 14. The palatometer 12 also preferably includes a microphone 32 to detect sounds made by the user.

A method for utilizing lingual movements to foster articulation change through modeling and mimicry will now be described. Preferably, a subject is fitted with a customized pseudopalate 14 that has an array of sensors 22 to detect lip and tongue contact. As the palatometer 12 is used, contact with the sensors 22 is detected and routed to the processing and display equipment 16. Prior to contact, the palate sensors 22 are preferably shown on the monitor as small black dots 34 within a grid array. The dots 34 are located on the screen such that their placement is accurately portrayed with respect to the dental and palatal configurations. Teeth 36 are represented as though the observer is looking upward from the tongue. The teeth 36 thus serve as natural orienting landmarks to help the observer focus on precisely how, when, and where articulation actions transpire in the mouth as different sounds are modeled and articulated. Images of the dots 34 are preferably expanded in size and the colors changed to blue to indicate sensor contact as indicated at 38. Each of the expanded dots 38 represent contact with a corresponding sensor 22, thus the boundaries, extent, and areas of contact can be quantified.

When palatometric data collection is activated, sensor contact may be collected and stored in computer memory, preferably at a 200 Hz rate for example. Parallel acoustic phonetic data is preferably captured and stored simultaneously. In a feedback mode of the palatometer, real-time side-by-side contact pattern displays are preferably generated from the model and learner responses at a 50 Hz rate. The model contact patterns are preferably drawn from the prerecorded utterances with accompanying acoustic playback provided to help the speech-impaired learner mimic both the visual and auditory model patterns precisely. The stimulus sounds, words, phrases, and sentences to be spoken are preferably printed below the palatal images.

In a redisplay or later analysis mode of the palatometer, articulation performance is preferably accompanied by a synchronized intensity by time waveform display. This permits cursor controlled stop motion or dynamic image slow motion displays referenced to the time continuum when the sounds were produced. Automatic data analysis routines convert this information into quantitative contact place, configuration and timing descriptions. This allows numerical scores to be generated to represent how closely a learner's responses imitate a model as it is mimicked. The scores rise toward 100% as the learner's responses approach a given modeled pattern. The numerical transformation thus fosters absolute mimicry through easily interpreted success reinforcement.

Preferably, the learner is guided to mimic spoken sounds, words, and phrases from a model speaker, also referred to as an optimal speaker. The model speaker may be representative of a particular group, such as a particular age, gender, language type or any other category desired for the learner to mimic known to those skilled in the art. Preferably, visual mimicry accuracy is analyzed with respect to the match between the learner and the model. Visual mimicry accuracy may be analyzed with respect to the match between the modeled and mimicked linguapalatal contact place and timing during a given response. A numerical score may then be derived and displayed on the computer monitor that represents the closeness of contact pattern fit achieved in each learner response. The visual feedback may be supplemented by learning curves that show mimicry accuracy for a given stimulus over time. Score improvements may be reinforced by written, computer generated congratulations and by dynamic displays on the computer monitor following successful responses for example.

Auditory mimicry accuracy may be analyzed acoustically, and a numerical score derived and displayed on the computer monitor that represents the closeness of acoustic fit achieved in each of the learner's responses. The auditory feedback may be supplemented by sound spectrographic displays generated from the model stimuli and the mimicked responses. The numerical measure of improvement may be plotted in learning curves that show mimicry accuracy for a given stimulus over time. Score improvements may also be reinforced by computer generated audible congratulations and by dynamic displays on the computer monitor following successful responses.

Situations in which target mimicry may be beneficial include for example: children unable to overcome speech disorders through traditional, auditory based therapy; those born with severe to profound hearing losses, including those who are deaf; persons with stroke-limited ability to control tongue movement and placement; persons with hearing loss limited high frequency sound perception which causes lisping, "s" sound distortions and substitutions; persons with reduced ability to build up pressure in the mouth (e.g. from problems such as velopharyngeal incompetence related to palate clefts, submucous clefts, short palates, etc.); persons with maladaptations to physical abnormalities affecting the mouth and other parts of the vocal tract (e.g. prolonged loss of teeth in the developing child or adult, adjustments to malfitting dentures); guiding speakers to better ways to conserve a limited air supply (e.g. to develop and facilitate esophageal speech after laryngectomy, to conserve air after it has been reduced by chest or diaphragm injury or when a patient's physical condition limits the energy that can be devoted to speech activity); persons needing to learn new speech patterns after cochlear implant surgery; people with gradually deteriorating hearing loss who need help to maintain speech articulation skills; persons that can't discover from hearing alone how they are misarticulating sounds (e.g. foreign or regional dialects).

Thus, a method for providing speech therapy includes displaying a model representation of a position of contact between a model tongue and mouth during speech; displaying a representation of a position of contact between a learner's tongue and mouth during speech; and instructing the learner to mimic the model representation. The representation of the position of contact between the learner's tongue and mouth during speech is compared with the model, and the closeness of the match is mathematically quantified as a score.

Lingual movements may also be used to assess the proficiency of speech. Since speech represents the output from a complex biological and phonological system, multiple sources of articulatory deviation may be expected. A long accepted general hypothesis among speech pathologists is that articulatory disorders are products of experiential and physical conditions that block a learner from achieving normal sound production proficiency. The tests and measures, as described below, have been developed to help pinpoint possible sources of such deviations.

One manner in which the proficiency of speech may be assessed includes assessment of lingual movements during vowel articulation. For example, measures may be obtained from repetitions of vowels (V) in isolation, and in the context with consonants (C) such as CVC, where C is a stop consonant(p, t, or k) or a fricative consonant(a consonant, such as s, produced by the forcing of breath through a constricted passage) such as in the sentence or predetermined syllable set "have a CVC away." As those skilled in the art will recognize, various different predetermined syllable sets may be used within the scope of the present invention. Preferably, the participant repeats the predetermined syllable set as naturally as possible. Palatometric parameters may then be measured for each vowel in each context. Palatometric parameters as referred to herein are defined as measurements which describe the vocal process during speech as measured by an instrument such as a palatometer. For example, palatometric parameters include time from vowel onset to offset, jaw separation at vowel midpoint, distance between the most anterior palatometric sensor contacted and the central incisor edge 40, distance laterally between the innermost sensor contacted and the dental margin 42, palatal surface area contacted, channel width at its narrowest point between the sensors, distance from the front sensor contacted to the central incisor tip sensors 44, mid-sagittal distance (measured by the two rows of sensors 46 that are immediately adjacent the mid line) between front and back sensor contacts during stop consonants, width of the stricture opening during speech of fricatives, affricatives (composite speech sounds consisting of a stop and a fricative articulated at the same point, as "ch" in "chair" and "j" in "joy") and laterals (sounds produced by breath passing along one or both sides of the tongue, such as in "l"), or any other measurement known to those skilled in the art which is suitable for comparing speech of different speakers. The palatometric parameters measured may be compared to a standard to assess the speech of an individual.

Similarly, consonant articulation may be assessed by repeating different kinds of consonants such as nasal (articulated by lowering the soft palate so that air resonates in the nasal cavities and passes out the nose, as in the pronunciation of the nasal consonants m, n, and ng), stop, fricative, affricates and approximant consonants. Each sound may be tested in isolation and in a point vowel context such as in the predetermined syllable set "have a VCV away," spoken as naturally as possible. Applicable palatometric parameters, as discussed above, may be measured during repetition of the consonants for comparing with a standard to assess the speech of the individual.

Another manner in which lingual movements may be used to assess speech includes the palatometric target to target movement tracking paradigm, used to help define lingual motor skill. Preferably, tongue tip placement at a preestablished target point in the 3-dimensional Euclidean space around the dental-gingival surface is established. Tongue tip movement velocity, time lapse and placement accuracy may then be measured as the testee moves the tongue in a random order from this point to other points along the dental-gingival border. The resultant data may be logged in a computer file for later analysis and also summarized in computer screen displays. The purpose of the numerical feedback in the displays is to encourage the testee's best effort, to reinforce performance improvements, and to examine possible differential changes in lingual manipulation proficiency as a function of the target-to-target test experience.

The location of the targets and the initiation of the start signal may be generated by computer software or a practitioner for example. The results of the target to target analysis may be compared to a standard, earlier results from the testee, or another person for example.

The ability to identify, gauge, and classify lingual control numerically may enhance the ability to identify motor-control irregularities and abnormalities. This information may also be used to help isolate specific lingual movement skill deviations that might influence articulation mimicry. Additionally, the databased information may help explain differences found in articulation skill change through acoustic and/or linguapalatal contact visual mimicry. Another valuable tool for assessing the proficiency of speech is the maximum syllable repetition rate. Disturbances affecting syllable repetition rate include for example: slow rate from oral motor control immaturity (younger children have slower rate); slow rate from paralysis or paresis (weakness) of the speech articulators; variable rate from discoordination; slowing or drifting from maximum rate from attention deficit or concentration loss; and breaks in rhythm from reduced speech motor control. The detection of oral movements may be used to more efficiently establish a participant's repetition skill. Preferably, the number of predetermined syllable sets, for example pa, ta, ka, pata, taka, or pataka, repeated during a standard response period, preferably five second, is established. As those skilled in the art will appreciate, other predetermined syllable sets and response periods may be used within the scope of the present invention. The time lapse measures may begin at the moment the initial consonant contact is released at the lips, tip of tongue, and/or back of the tongue. The syllable repetition rate may then be calculated and automatically printed out by syllable across the complete syllable set and a general score derived. A number of secondary measures such as response rate variability, rhythm disturbances, rate slowing, and drifting toward imprecise sound patterns may also be generated. These maximum syllable repetition rate measures, along with the target-to-target motor control measures, provide a rich set of observations to evaluate possible motor skill, coordination deviation, and motor impairment among the normal speaking and articulatory impaired individuals.

Another tool which may be used to assess speech is the voice onset time (VOT) assessment, or measurement of the time lapse between a stop consonant articulatory release moment and the voicing onset of the following vowel. An example of the stop consonant articulatory release moment is the moment the tongue is released from the palate to make a "t" sound. While VOT has been measured acoustically, the consonant release may produce only a brief, difficult to detect, low intensity noise. Oral movements may be detected to eliminate the uncertainties of acoustic VOT measures. Among the benefits from the present invention is that VOT values may now be easily, accurately, and automatically obtained.

To determine the VOT values for a testee, the testee is fitted with a sensor plate 14 of the palatometer 12 and instructed to speak an utterance. Preferably the testee is instructed to read five randomized sets of 12 vowel-consonant-vowel (VCV) words embedded in the sentence "Have a VCV away." The representation C=/p/, /b/, /t/,/d/, /k/, or /g/, V= /i/ or /u/) is intended to indicate sets of consonants and vowels from which vowel-consonant-vowel speech clusters can be formed for such exercises, wherein "C" means "consonant" and "V" means "vowel." For example, the speech clusters "ibi," "udu" and "iki" could be selected, as well as several others.

As those skilled in the art will recognize, other sets of vowels, consonants, words, and sentences may be used within the scope of the present invention. The acoustics are detected through the microphone 32 and the oral movements are detected by the palatometer. The mean time lapse from stop consonant constriction release moment, as detected by the oral movements, to the acoustically detected quasiperiodic vocal fold vibration onset denoting the vowel steady state may then be established for each utterance set. These values may be analyzed to determine and compare differences in the VOT scores with other VOT scores such as a standard, a particular age or gender, or other desired representation.

Another advantage of the present invention is that lingual mobility may be enhanced. For example, in the event an individual has a condition which affects the speech, such as the removal of a portion of the tongue, the individual may view palatometric data from others who overcame a similar condition to see how lingual movements may be altered to compensate for the condition. In this manner, compensatory tongue postures may be developed. Similarly, a practitioner may develop tongue exercises to assist in the enhancement of lingual mobility. Examples of circumstances where tongue exercises may be beneficial include: weakness following stroke; improving tongue movement precision related to cerebral palsy and other neurological disorders; helping to recover from chewing and swallowing impairment (e.g. from lingual tissue excision incident to surgery from vocal tract cancer, full mouth dental extraction, car or other accidental damage); and person such as trumpet player who wants to increase lingual dexterity.

The individual is instructed to perform a lingual movement which is designed to enhance lingual mobility or speech. Representations of a position of contact between the tongue and mouth are displayed so that the individual can see how to position the tongue. The individual can then repeat the lingual movements to improve the individual's speech.

Oral movements can also be used to exert control over external devices having electronic controls. Electronic controls as referred to herein include any system, known to those skilled in the art, for manipulating a device which can be activated electronically. For example, wheel chairs may be operated by electronic controls. The electronic controls may be connected to a sensor plate 14 so that oral movements can operate the wheelchair. This arrangement is beneficial to those who would otherwise be unable to operate the wheelchair. A contact point may be established on a particular area of the sensor plate 14 to operate a particular function. For example, contact points may be established on the front, back, left, and right sides of the sensor plate 14 to operate forward, reverse, left turn and right turn functions respectively. As those skilled in the art will recognize, one or a plurality of contact points may be established in various locations on the sensor plate 14 to operate numerous different functions of external devices. The user may simply touch a contact point with the tongue wherein the flow of electricity through the tongue and the contact point (sensors 22) on the sensor plate 14 activates the wheelchair. Electronic games, devices producing depictions of cartoon mouth movements, and other devices known to those skilled in the art may also be controlled by lingual movements in a similar fashion.

In view of the foregoing, it will be appreciated that the present invention provides a method for utilizing lingual movements which allows speech therapy through visual modeling and mimicry. The present invention also provides a method for utilizing lingual movements for speech assessment and enhancement of lingual mobility. The methods provided herein are advantageous for those with speech problems, the hearing impaired, as well as those learning foreign languages. The present invention also provides for utilizing lingual movements to control external devices.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for providing speech therapy comprising:
   (A) displaying a model representation of a position of contact between a model tongue and mouth during speech;
   (B) displaying a representation of a position of contact between a learner's tongue and mouth during speech;
   (C) displaying a model representation of a contact between a model lip and teeth during speech; and
   (D) representing the position of contact between the learner's tongue and mouth during speech by a grid of dots on a computer screen, wherein said dots expand and change color responsive to contact between the learner's tongue and mouth.

2. The method of claim 1 further comprising instructing the learner to mimic the model representation of the position of contact between the model tongue and mouth during speech.

3. The method of claim 2 further comprising the step of comparing the representation of the position of contact between the learner's tongue and mouth during speech with the model representation of position of contact between the model tongue and mouth during speech.

4. The method of claim 2 further comprising the step of generating a numerical score representing the closeness of fit between the representation of position of contact between the learner's tongue and mouth during speech and the model representation of position of contact between the model tongue and mouth during speech.

5. The method of claim 2 further comprising the step of providing positive reinforcement when the learner mimics the model representation of position of contact between the model tongue and mouth during speech.

6. The method of claim 5 wherein the positive reinforcement comprises computer generated congratulations.

7. The method of claim 5 wherein the positive reinforcement comprises dynamic displays on a computer monitor.

8. The method of claim 2 further comprising the step of providing model acoustic representations of the speech.

9. The method of claim 8 wherein auditory mimicry accuracy between the learner and the model acoustic representation are analyzed acoustically.

10. The method of claim 9 wherein a numerical score representing the closeness of acoustic fit is generated.

11. The method of claim 8 wherein sound spectrographic displays are generated from the model acoustic representation and the learner's speech.

12. The method of claim 2 wherein the model representation is designed to exercise the learner's tongue when the learner mimics the model representation.

13. The method of claim 2 wherein the model representation is designed to instruct the learner to compensate for physical deficiencies.

14. The method of claim 1 wherein the representations of position of contact between the learner's tongue and mouth during speech and the model representations of position of contact between the model tongue and mouth during speech are displayed on a split-screen.

15. The method of claim 1 wherein the learner is unable to overcome speech disorders through traditional auditory based therapy.

16. The method of claim 1 wherein the learner has severe to profound hearing loss.

17. The method of claim 1 wherein the learner has stroke-limited ability to control tongue movement and placement.

18. The method of claim 1 wherein the learner has limited high frequency sound perception which causes lisping.

19. The method of claim 1 wherein the learner has reduced ability to build up pressure in the mouth.

20. The method of claim 1 wherein the learner has physical abnormalities affecting the mouth and vocal tract.

21. The method of claim 1 wherein the learner has limited energy to devote to speech activity.

22. The method of claim 1 wherein the learner is learning new speech patterns after cochlear implant surgery.

23. The method of claim 1 wherein the learner has gradually deteriorating hearing loss and needs assistance to maintain speech articulation skills.

24. The method of claim 1 wherein the learner is learning a speech pattern selected from the group consisting of a foreign language and a dialect.

25. The method of claim 1 wherein the grid of dots corresponds to sensors disposed on a sensor plate which is custom fitted in the mouth of the learner.

26. The method of claim 1 wherein the speech includes sounds, words, phrases or sentences, and wherein the sounds, words, phrases, or sentences are displayed in writing.

27. The method of claim 1 wherein the position of contact between the learner's tongue and mouth during speech is recorded.

28. The method of claim 27 wherein the learner's speech is recorded acoustically corresponding to the position of contact between the learner's tongue and mouth during speech.

29. The method of claim 27 wherein the model representation is recorded.

30. The method of claim 1 wherein the model representation is generated by a model speaker.

31. The method of claim 30 wherein the model speaker is representative of a particular age group, gender, or language type.

32. The method of claim 1 further comprising:
(E) displaying a representation of a contact between a learner's lip and teeth during speech.

33. A method for providing speech therapy comprising:
(A) displaying a model representation of a position of contact between a model tongue and mouth during speech;
(B) displaying a representation of a position of contact between a learner's tongue and mouth during speech;
(C) instructing the learner to mimic the model representation of the position of contact between the model tongue and mouth during speech;
(D) comparing the representation of the position of contact between the learner's tongue and mouth during speech with the model representation of position of contact between the model tongue and mouth during speech;
(E) generating a numerical score representing the closeness of fit between the representation of position of contact between the learner's tongue and mouth during speech and the model representation of position of contact between the model tongue and mouth during speech;
(F) providing positive reinforcement when the learner mimics the model representation of position of contact between the model tongue and mouth during speech; and
(G) providing model acoustic representations of the speech;
wherein the representations of position of contact between the learner's tongue and mouth during speech and the model representations of position of contact between the model tongue and mouth during speech are displayed on a split-screen;
wherein auditory mimicry accuracy between the learner and the model acoustic representation are analyzed acoustically;
wherein a numerical score representing the closeness of acoustic fit is generated;
wherein sound spectrographic displays are generated from the model acoustic representation and the learner's speech;
wherein the position of contact between the learner's tongue and mouth during speech is represented by a grid of dots on said split-screen, said dots expand and change color corresponding to contact between the learner's tongue and mouth;
wherein a dental landmark is displayed on the split-screen to help orient the position of contact between the learner's tongue and mouth;
wherein the grid of dots corresponds to sensors disposed on a sensor plate which is custom fitted in the mouth of the learner;
wherein the speech includes sounds, words, phrases or sentences, and wherein the sounds, words, phrases, or sentences are displayed in writing;
wherein the position of contact between the learner's tongue and mouth during speech is recorded;
wherein the learner's speech is recorded acoustically corresponding to the position of contact between the learner's tongue and mouth during speech;
wherein the method further comprises displaying a model representation of a contact between a model lip and teeth during speech;
wherein the method further comprises displaying a representation of a contact between a learner's lip and teeth during speech; and
automatically generating learning curve plots illustrating the ability of the learner to mimic the contact of the model tongue and mouth and the model lip and teeth.

34. A method for providing speech therapy comprising:
(A) displaying a model representation of a position of contact between a model tongue and mouth during speech;
(B) displaying a representation of a position of contact between a learner's tongue and mouth during speech;
(C) instructing the learner to mimic the model representation of the position of contact between the model tongue and mouth during speech;

(D) measuring palatometric parameters of the learner; and (E) displaying a model representation of a contact between a model lip and teeth during speech.

35. The method of claim 34 further comprising:

displaying a dental landmark on the computer screen to assist in orienting the contact between the learner's tongue and mouth.

36. The method of claim 34 further comprising:

automatically generating learning curve plots illustrating the ability of the learner to mimic the model.

37. The method of claim 34 further comprising:

displaying a representation of a contact between a learner's lip and teeth during speech.

* * * * *